United States Patent
Pohrte et al.

(10) Patent No.: US 10,085,473 B2
(45) Date of Patent: *Oct. 2, 2018

(54) PURIFICATION OF LUO HAN GUO EXTRACT

(71) Applicant: Tate & Lyle Ingredients Americas LLC, Hoffman Estates, IL (US)

(72) Inventors: Brian Pohrte, Hoffman Estates, IL (US); Timothy C. Schunk, Hoffman Estates, IL (US); Elber F. Tejada, Hoffman Estates, IL (US)

(73) Assignee: TATE & LYLE INGREDIENTS AMERICAS LLC, Hoffman Estates, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/272,634

(22) Filed: Sep. 22, 2016

(65) Prior Publication Data

US 2017/0035085 A1 Feb. 9, 2017

Related U.S. Application Data

(60) Continuation of application No. 14/215,647, filed on Mar. 17, 2014, now Pat. No. 9,474,295, which is a division of application No. 13/355,852, filed on Jan. 23, 2012, now Pat. No. 8,962,698.

(60) Provisional application No. 61/437,399, filed on Jan. 28, 2011.

(51) Int. Cl.
*A23L 27/30* (2016.01)
*A23L 27/10* (2016.01)
*A23L 27/16* (2016.01)

(52) U.S. Cl.
CPC ............ *A23L 27/33* (2016.08); *A23L 27/10* (2016.08); *A23L 27/36* (2016.08); *A23V 2002/00* (2013.01)

(58) Field of Classification Search
None
See application file for complete search history.

(56) References Cited

U.S. PATENT DOCUMENTS

| | | |
|---|---|---|
| RE30,820 E | 12/1981 | Walon |
| 5,411,755 A | 5/1995 | Downton |
| 5,433,965 A | 7/1995 | Fischer |
| 5,690,725 A | 11/1997 | Tucker |
| 5,756,721 A * | 5/1998 | Eden ............ C07H 1/08 536/102 |
| 6,335,461 B1 | 1/2002 | Amino |

(Continued)

FOREIGN PATENT DOCUMENTS

| | | |
|---|---|---|
| CN | 1094892 | 11/1994 |
| CN | 101007042 A | 8/2007 |

(Continued)

OTHER PUBLICATIONS

European Examination Report for European Application No. 12702707.6, dated May 20, 2016, 7 pages.

(Continued)

*Primary Examiner* — Ernst V Arnold
*Assistant Examiner* — Kyung S Chang
(74) *Attorney, Agent, or Firm* — RatnerPrestia

(57) ABSTRACT

A method of purifying a Luo Han Guo extract includes contacting the Luo Han Guo extract with activated carbon and a macroporous polymeric adsorbent resin, an ion exchange resin, or both.

20 Claims, 6 Drawing Sheets

(56) References Cited

U.S. PATENT DOCUMENTS

| | | |
|---|---|---|
| 7,575,772 B2 | 8/2009 | Shi |
| 7,815,956 B2 | 10/2010 | Lee |
| 7,884,265 B2 | 2/2011 | Morita |
| 9,044,038 B2 | 6/2015 | Yoshinaka et al. |
| 2005/0152997 A1 | 7/2005 | Selzer |
| 2006/0003053 A1 | 1/2006 | Ekanayake |
| 2007/0116823 A1 | 5/2007 | Prakash |
| 2007/0116828 A1 | 5/2007 | Prakash |
| 2007/0116836 A1 | 5/2007 | Prakash |
| 2007/0116839 A1 | 5/2007 | Prakash |
| 2007/0116840 A1 | 5/2007 | Prakash |
| 2007/0224292 A1 | 9/2007 | Brunner |
| 2008/0107775 A1 | 5/2008 | Prakash |
| 2008/0226788 A1 | 9/2008 | Chang |
| 2008/0226796 A1 | 9/2008 | Lee |
| 2008/0274258 A1 | 11/2008 | Shi |
| 2008/0292775 A1 | 11/2008 | Prakash |
| 2008/0299277 A1 | 12/2008 | Chao |
| 2009/0162487 A1 | 6/2009 | Bell |
| 2009/0196966 A1 | 8/2009 | West |
| 2010/0099857 A1 | 4/2010 | Evans |
| 2010/0112154 A1 | 5/2010 | Abelyan |
| 2010/0233322 A1 | 9/2010 | Fukuda |
| 2010/0267847 A1 | 10/2010 | Yoshinaka |
| 2010/0285195 A1 | 11/2010 | Fisher |
| 2010/0316782 A1 | 12/2010 | Shi |
| 2011/0021456 A1 | 1/2011 | Lyndon |
| 2011/0023192 A1 | 1/2011 | Morita |
| 2011/0038957 A1 | 2/2011 | Fowler |
| 2011/0052755 A1 | 3/2011 | Fiorenza |
| 2011/0091394 A1 | 4/2011 | Abelyan |
| 2011/0287164 A1 | 11/2011 | Markosyan |
| 2012/0059071 A1 | 3/2012 | Markosyan |
| 2012/0183648 A1 | 7/2012 | Sun |
| 2012/0264831 A1 | 10/2012 | Bridges |
| 2012/0289687 A1 | 11/2012 | Erickson |
| 2013/0071537 A1 | 3/2013 | Shi |
| 2013/0136838 A1 | 5/2013 | San Miguel |
| 2013/0164420 A1 | 6/2013 | Catani |
| 2013/0309389 A1 | 11/2013 | Carlson |
| 2015/0216209 A1 | 8/2015 | Lyndon |

FOREIGN PATENT DOCUMENTS

| | | |
|---|---|---|
| CN | 101167539 | 4/2008 |
| CN | 101327244 | 12/2008 |
| CN | 101690573 | 4/2010 |
| CN | 101711926 | 5/2010 |
| CN | 101731493 A | 6/2010 |
| CN | 101863946 | 10/2010 |
| CN | 201682999 | 12/2010 |
| CN | 102060892 | 5/2011 |
| CN | 102093445 | 6/2011 |
| CN | 102093447 | 6/2011 |
| EP | 0945074 | 9/1999 |
| EP | 2215914 | 8/2010 |
| EP | 2425721 | 3/2012 |
| EP | 2486806 | 8/2012 |
| JP | 52083731 | 7/1977 |
| JP | S5283986 | 7/1977 |
| JP | S5312466 | 2/1978 |
| JP | S5871868 | 4/1983 |
| JP | 08506733 | 7/1996 |
| JP | 11046701 | 2/1999 |
| JP | 2000287642 | 10/2000 |
| JP | 2003274911 | 9/2003 |
| JP | 3547553 | 7/2004 |
| JP | 2009269912 | 11/2009 |
| JP | 2010502213 | 1/2010 |
| KR | 100888694 B1 | 3/2009 |
| KR | 1020100094505 A | 8/2010 |
| RU | 2160310 | 12/2000 |
| WO | 199418854 | 9/1994 |
| WO | 2006093229 | 9/2006 |
| WO | 2008030121 | 3/2008 |
| WO | 2008091547 | 7/2008 |
| WO | 2008112991 | 9/2008 |
| WO | 2009006208 | 1/2009 |
| WO | 2009016374 | 2/2009 |
| WO | 2009044559 | 4/2009 |
| WO | 2009063921 | 5/2009 |
| WO | 2009071277 | 6/2009 |
| WO | 2009086049 | 7/2009 |
| WO | 2009093610 | 7/2009 |
| WO | 2010038911 | 4/2010 |
| WO | 2011066754 | 6/2011 |
| WO | 2011094423 | 8/2011 |
| WO | 2012082677 | 6/2012 |
| WO | 2012088598 | 7/2012 |
| WO | 2012103074 | 8/2012 |
| WO | 2012108894 | 8/2012 |
| WO | 2012109506 | 8/2012 |
| WO | 2012109585 | 8/2012 |
| WO | 2012125991 | 9/2012 |
| WO | 2012166163 | 12/2012 |
| WO | 2012166164 | 12/2012 |
| WO | 2012177727 | 12/2012 |
| WO | 2013036366 | 3/2013 |
| WO | 2013036768 | 3/2013 |

OTHER PUBLICATIONS

Australian Examination Report for Australian Application No. 2015261566, dated May 30, 2016, 5 pages.

"Lovia", Layn Natural Ingredients, http://www.layncorp.com/showproducts.php?id=126, accessed on Jan. 20, 2012, 2 pgs.

"Layn's Luo Han Guo Natural Sweetener has acheived GRAS status", Lovia, Taking Stevia to the Next level, Layn Natural Ingredients, http://www.layncorp.com/news.php (May 1, 2011), 1 pg.

Gelski, Jeff, "Sweetner Combines Stevia, Luo Han Guo Fruit", FoodBusinessNews.net (Jun. 13, 2011), 1 pg.

Mosciano, Gerard, "Developing a Common Language Between Flavorists and Product Developers", Perfumer & Flavorist, vol. 25, (Mar./Apr. 2000) 6 pgs.

Schiffman, S. S., "Investigation of Synergism in Binary Mixtures of Sweeteners", Brain Research Bulletin, vol. 38, No. 2, (Jan. 20, 1995), pp. 105-120.

Schiffman, Susan S., "Synergism among Ternary Mixtures of Fourteen Sweeteners", Chem. Senses 25, (2000) pp. 131-140.

Notification of International Preliminary Report on Patentability and Written Opinion issued for PCT/US2012/022339 dated Aug. 8, 2013, 10 pages.

International Search Report dated Sep. 27, 2012, Int'l Appl. No. PCT/US2012/022339, 6 pages.

Partial International Search Report dated Jun. 22, 2012 for PCT/US2012/022339, 2 pages.

Chinese Office Action dated Dec. 24, 2014 in related Application No. 201280010780.7, 13 pages.

Office Action dated Mar. 3, 2015, in U.S. Appl. No. 13/956,996, 29 pages.

Japanese Informative Statement dated Jan. 30, 2015 in Japanese Application No. 2013-551285, 5 pages.

Australian Examination Report dated Mar. 17, 2015 for Australian Application No. 2012209241, 5 pages.

Japanese Notice of Reasons for Rejection dated Jun. 30, 2015 for Japanese Application No. 2013-551285, including English translation, 11 pages.

Russian Office Action dated Nov. 9, 2015 in Russian Application No. 2013139876/13(060475), including English language translation, 10 pages.

Japanese Office Action dated Feb. 16, 2016 for Japanese Application No. 2013-551285 with translation, 12 pages.

Indonesian Office Action dated Jan. 20, 2016 for Indonesian Application No. W-00201303932, 3 pages.

Chinese Office Action dated Jul. 1, 2014 in related Application No. 201180069627.7, 17 pages.

(56) References Cited

OTHER PUBLICATIONS

Compounds (C26H30O10) provided by Chemspider (http://www.chemspider.com/Search.aspx?rid=5a954e4d-a6f4-41f8-b7d0-1b2e5cea4bba), downloaded on Apr. 2, 2013, 10 pages.
International Search Report and Written Opinion issued for International Application No. PCT/US2013/052821, dated Oct. 30, 2013, 10 pages.
Kinghorn et al., Studies to Identify, Isolate, Develop and Test Naturally Occurring Noncariogenic Sweeteners that May be used as Dietary Sucrose Substitutes, Comprehensive Technical Report for the Period Jun. 25, 1980-Sep. 24, 1983, 35 pages.
Kohda et al., "New Sweet Diterpene Glucosides from Stevia Rebaudiana," Phytochemistry, 1976, pp. 981-983, vol. 14.
Mizukami et al., "Enzymatic Determination of Stevioside in Stevia Rebaudiana," Phytochemistry, 1982, pp. 1927-1930, vol. 21, No. 8.
UKIPO Combined Search and Examination Report issued for Application No. GB1217700.2 dated Jan. 29, 2013, 6 pages.
Yuqiang et al., "Production of B-fructofuranosidase and Optimization of Enzymatic Modification Process for Stevioside and Rebaudioside A," Food and Fermentation, vol. 35, issue 03, pp. 23-27, Dec. 21, 2009: Abstract Only.
Extended European Search Reort for European Application No. 16181751.5, dated Nov. 22, 2016, 10 pages.
Japanese Office Action for Japanese Application No. 2015-207779, dated Oct. 25, 2016 with translation, 13 pages.
Chinese Office Action for Application No. 201510541887.X, dated Mar. 24, 2017 with translation, 19 pages.
Korean Office Action for Korean Application No. 10-2013-7022796, dated Apr. 24, 2017, including English translation, 21 pages.
Guon et al., Journal of Guangdong Pharmaceutical College, Aug. 2010, vol. 26, No. 4, pp. 351-354 (with English abstract ).
Wang, et al., Chinese Pharmaceutical Journal, 2007, vol. 42, No. 9, pp. 702-705 (with English abstract).
Abe, Kankyo-Gijutsu (Japanese Journal: Journal of Environmental Conservation Engineering), 1991, vol. 20, No. 6, pp. 27-32.
Notification of Reasons for Rejection for Japanese Application No. 2017-010434, dated Jan. 30, 2018, (with English translation), 6 pages.
Notice of Reasons for Rejection for Japanese Application No. 2015-207779, dated Jan. 16, 2018, including English translation, 5 pages.
Eisei, S., Journal of Urban Living and Health Association, 1993, vol. 37, pp. 163-170 (partial English Translation).

\* cited by examiner

PURIFICATION OF LUO HAN GUO EXTRACT

CROSS REFERENCE TO RELATED APPLICATIONS

This application is a continuation of U.S. application Ser. No. 14/215,647, filed Mar. 17, 2014, which claims priority from U.S. application Ser. No. 13/355,852, filed Jan. 23, 2012, now U.S. Pat. No. 8,962,698, issued Feb. 24, 2015, which claims priority from U.S. provisional application 61/437,399, filed Jan. 28, 2011, the entire contents of which are hereby incorporated herein by reference for all purposes.

BACKGROUND

Natural caloric sweeteners, such as sucrose, glucose, and fructose, possess desirable taste characteristics, but they add to the caloric content of products. Therefore, there is great consumer interest in low or non-caloric sweeteners that are considered as healthier alternatives. Non-caloric natural and synthetic high-potency sweeteners are known, but they most often possess flavor profiles that are not as desirable to consumers as sugars. Thus, it is desirable to develop non-caloric sweeteners that can be substituted for sugar and that have a more desirable taste profile.

The species *Stevia rebaudiana* ("*Stevia*") is the source of certain naturally occurring sweet steviol glycosides. Considerable research and development has been done to evaluate the use of sweet steviol glycosides of *Stevia* as non-caloric sweeteners. Sweet steviol glycosides that may be extracted from *Stevia* include the six Rebaudiosides (i.e., Rebaudiosides A to F), stevioside (the predominant glycoside in extracts from wild type *Stevia*), steviolbioside, rubusoside, and dulcosides.

Commercial low or non-caloric sweeteners based on Rebaudioside A and other sweet steviol glycosides tend to have bitter and liquorice aftertastes. These characteristics are especially notable at concentrations above about 300 ppm. In food applications, preferred use levels (8-10% sugar equivalence values) are typically about 500 ppm to about 1000 ppm, above the range at which off tastes are first noticed. Thus a need continues to exist for reduced-, low-, and/or non-caloric sweeteners including sweet steviol glycosides that have taste profiles with reduced or no bitterness, undesirable flavors (e.g., licorice), or sweetness profiles more like natural caloric sweeteners, or combinations of such properties.

SUMMARY OF THE INVENTION

In one aspect, the invention provides a composition including Mogroside V and a Rebaudioside component in a weight ratio ≥1:1 and ≤6:1, wherein the Rebaudioside component consists of one or more compounds selected from the group consisting of Rebaudioside A, Rebaudioside B and Rebaudioside D.

In another aspect, the invention provides a method of purifying a Luo Han Guo extract that includes contacting the Luo Han Guo extract with activated carbon and a macroporous polymeric adsorbent resin, an ion exchange resin, or both.

In yet another aspect, the invention provides a composition including a Luo Han Guo extract, wherein Mogroside V constitutes from 50 wt % to 75 wt % of the Luo Han Guo extract and the composition includes from 0 to 13 wt % in total relative to the Mogroside V of aromatic glycosides, and from 0 to 15 ppm of semi-volatile organic compounds relative to the Mogroside V.

DETAILED DESCRIPTION OF THE INVENTION

Definitions

Figure 1:
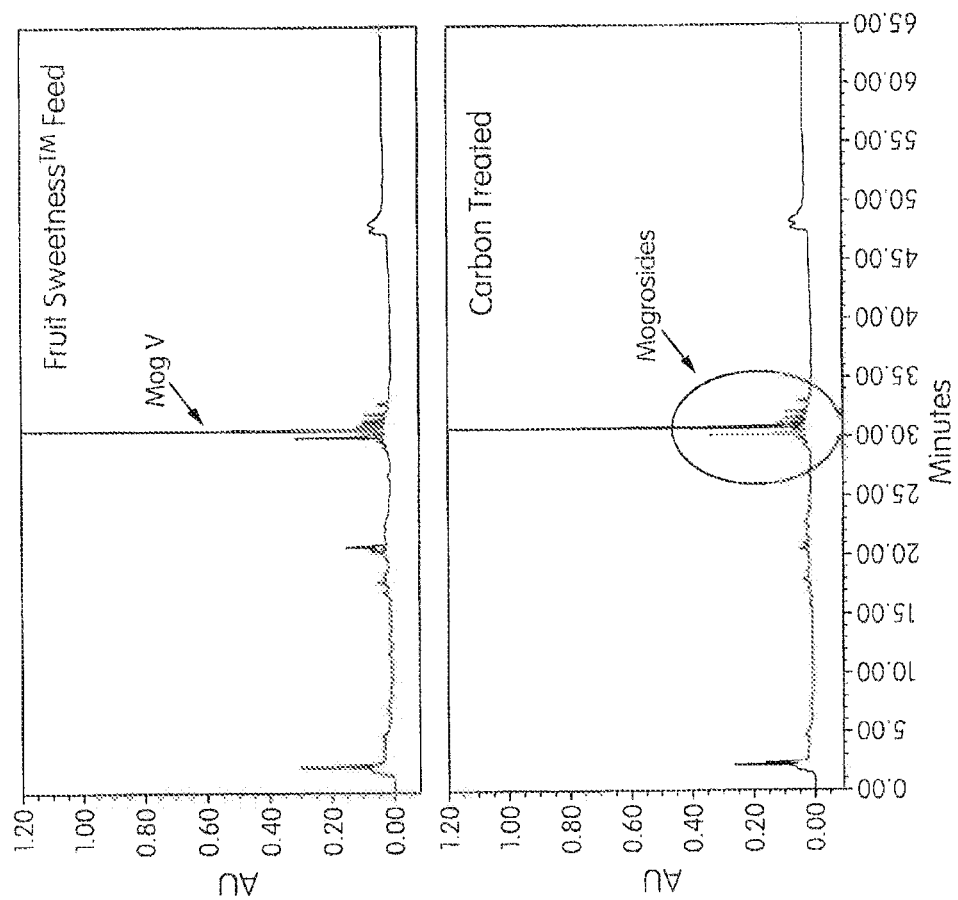
FIG. 1 shows HPLC analysis of an exemplary dry Luo Han Guo extract, and analysis of the same material that had been carbon treated according to the invention, in the upper and lower chromatograms respectively.

As used herein, the phrase "sweet steviol glycoside" means any naturally occurring compound having the general structure of a steviol diterpene ring system with one or more saccharide residues chemically attached to the ring.

As used herein, the phrase "Rebaudioside component" means the total of Rebaudioside A, B, and D present, with the understanding that only one or two of these may in fact be present.

Sweetening Compositions Including Rebaudioside-Mogroside V Blends

It is now disclosed that blends of Mogroside V with a Rebaudioside component consisting of one or more of Rebaudiosides A, B and D provide superior flavor characteristics, in many cases superior to either the Rebaudioside component or the Mogroside V alone, when compared at an equal level of sweetness. In some systems, the improved taste is most evident at pH values from about pH 2 to about pH 8.

Mogroside V may be obtained from extracts of Luo Han Guo, available commercially from a number of sources. Exemplary methods of producing such extracts are described in U.S. Pat. No. 5,411,755 and U.S. Publn. No. 2006/0003053, both incorporated herein by reference for all useful purposes. Luo Han Guo is extracted from the fruit of *Siraitia grosvenorii*, an herbaceous perennial vine native to southern China and Northern Thailand. It is one of four species in the genus *Siraitia*. Botanical synonyms include *Momordica grosvenorii* and *Thladiantha grosvenorii*. The extract is approximately 200-300 times as sweet as sucrose.

Typically, Mogroside V is the most abundant single Mogroside component of Luo Han Guo extracts, accompanied by other Mogrosides such as Mogrosides I, II, III, IV and VI as well as other extracted materials, such as polyphenols, flavonoids, melanoidins, terpenes, proteins, sugars, aromatic glycosides, and semi-volatile organic compounds. In some embodiments of the invention, the Mogroside V is provided in the form of a Luo Han Guo extract (either raw or purified and/or concentrated to increase Mogroside V content). In some embodiments, Mogroside V constitutes at least 40 wt % of the extract, or at least 45 wt %, or at least 50 wt %. Typically, it will constitute at most 95 wt % of the extract, at most 85 wt % of the extract, at most 75 wt % of the extract, at most 70 wt % of the extract, or at most 65 wt %, or at most 60 wt %.

In some sweetening compositions according to the invention, the weight ratio of Mogroside V to the Rebaudioside component is at least 1:1, or at least 1.3:1, or at least 1.5:1. The weight ratio is typically at most 5:1, or at most 4:1, or at most 3.5:1, or at most 3:1, or at most 2.5:1, or at most 2:1, or at most 1.9:1, or at most 18:1, or at most 1.7:1.

The Rebaudioside component consists of one or more of Rebaudioside A, B and/or D. The Rebaudioside component typically constitutes at least 65 wt % of the total sweet steviol glycosides present, or at least 70 wt %, or at least 75 wt %, or at least 80 wt %, or at least 90 wt %, or at least 97 wt %. The balance of sweet steviol glycosides, if any, may include one or more of Rebaudiosides C, E and/or F, stevioside, and any other sweet steviol glycoside not part of the Rebaudioside component. Typically, Rebaudioside A will constitute at least 50 wt % of the sweet steviol glycosides present, or at least 60 wt %, or at least 70 wt %, or at least 80 wt %, or at least 90 wt %, or at least 95 wt %. Rebaudioside A, B and D may be obtained from extracts of *Stevia rebaudiana*, available commercially from a number of sources. Many different methods of producing such extracts and obtaining relatively pure Rebaudioside A, B or D from the extracts are known and have been described in the literature, in one typical process, *stevia* plants are dried and subjected to a water extraction process. This crude extract contains about 50% Rebaudioside A. The various glycoside molecules in the extract are separated via crystallization techniques, typically using ethanol or methanol as solvent, permitting the isolation of pure Rebaudioside A, B and D. The individual purified glycosides may then be used in combination to provide Rebaudioside components useful in the present invention.

Although sweetening compositions of the invention may include mixtures of various types of sweeteners in various quantities, in some embodiments the composition consists essentially of an optionally purified and/or concentrated Luo Han Guo extract and an optionally purified and/or concentrated *Stevia* extract.

Removal of Off-Flavor Components of Luo Han Guo

It has now also been found, after extensive studies, that the presence of certain impurities in Luo Han Guo extracts results in an off-flavor described by some taste testers as "musty". In particular, aromatic glycosides and semi-volatile organic compounds have been identified as producing this undesirable flavor, although additional musty or other off-flavor components may also be present. One particular aromatic glycoside has a molecular mass of 502 Daltons, and appears to be particularly productive of the musty flavor. This compound is according to the formula $C_{26}H_{30}O_{10}$, and all compounds in total having this molecular formula are in some embodiments limited according to the invention. Any means of achieving a sufficiently low level of this compound is suitable for purposes of the invention. One suitable way is to pass an aqueous solution of the Mogroside V, for example in the form of an optionally purified and/or concentrated Luo Han Guo extract, through a column of granular activated carbon. Other forms of activated carbon, for example powders, may also be used. The carbon treatment also typically removes additional musty or other off-flavor components as well as pesticide residues and other such substances which are generally undesirable in ingredients intended for human consumption. Typically, water is the only carrier present during the carbon treatment, and no organic solvents are added. In some embodiments, the Luo Han Guo extract is treated with a macroporous polymeric adsorbent resin, an ion exchange resin, and the activated carbon. Typically the treatments will be in that order, but they need not be. One exemplary macroporous polymeric resin is available commercially from Rohm and Haas, Philadelphia, Pa. under the trade name AMBERLITE® XAD1180N. An exemplary suitable ion exchange resin is an anionic resin is available under the trade name AMBERLITE® FPA90 CL, also from Rohm and Haas.

The treatment must employ a sufficient amount of activated carbon, and must occur with a sufficiently long contact time, to reduce the level of the one or more aromatic glycoside and semi-volatile organic compound impurities to an acceptable level. In some embodiments of the invention the sweetening composition comprises from 0 to 13 wt % in total of aromatic glycosides, or from 0 to 11 wt %, or from 0 to 10 wt %, or from 0 to 9 wt %, all relative to Mogroside V. The aromatic glycosides may be phenyl glycosides or more specifically phenolic glycosides, or they may be coumarin glycosides or more specifically furanocoumarin glycosides. These same limits may also be appropriate in some embodiments for compounds of molecular mass 502, and more specifically for compounds according to the formula $C_{26}H_{30}O_{10}$, in each case referring to the total amount of all compounds of mass 502 or of formula $C_{26}H_{30}O_{10}$.

In some embodiments of the invention the sweetening composition comprises from 0 to 15 ppm wt in total of semi-volatile organic compounds, or from 0 to 11 ppm wt, or from 0 to 7 ppm wt, or from 0 to 3 ppm wt, all relative to Mogroside V. The term "semi-volatile" as used herein means compounds having a molecular weight in excess of 120 Daltons and a boiling point at 1 atm pressure greater than 150° C. and up to 350° C. Such semi-volatile organic compounds may comprise, but are not limited to, the compounds listed in Table 7. The semi-volatile organic compounds may for example include aliphatic furans, unsaturated aliphatics, esters, polycyclic hydrocarbons and/or terpenoids.

Commercially available Luo Han Guo powdered fruit extract, typically containing at least 40% of Mogroside V (d.s.b), may be treated with activated carbon as follows. Dry extract is dissolved in deionized water at a concentration of at least about 1 wt %, and typically at most about 70 wt %. The water is heated to a temperature sufficient to favor the dissolution of the powdered material, typically in a range between ambient temperature and 160° F. (71.1° C.), and optionally filtered using a microfiltration membrane or using filtration paper with a non reactive filtration aid. The purpose of the microfiltration is to remove insoluble proteins and/or microorganisms that could deteriorate the product. The resulting filtrate is subjected to adsorption with active carbon (also known as activated carbon). The carbon may be any form of active carbon available, and may for example be derived from wood, bituminous coal, lignite coal, coconut, bone char, or any other source. In one embodiment, the active carbon is obtained by steam activation of carbon from lignite coal. Typically, the carbon is in the form of granules, but other physical forms such as powders or bead activated carbon may also be employed. It will generally be advantageous to utilize an active carbon which is highly porous and which has a high surface area (e.g., over 100 $m^2/g$, over 200 $m^2/g$, or over 300 $m^2/g$). The non-desirable components causing the off-taste (as well as other undesirable substances such as pesticides) are adsorbed to the carbon, but the improved taste material is not adsorbed and is continuously eluted. The method allows for recovery yields (dry substance basis) between 50% and 99.9%. The amount of active carbon used may vary from 0.05% to 150% (as a percentage of the dry substance present in the aqueous solution of Luo Han Guo fruit extract). More typically, to achieve sufficiently low levels of off-taste components, at least 2 wt % or at least 5 wt % of activated carbon relative to Luo Han Guo fruit extract is used on a solids basis. In certain embodiments, at least 6 wt % or at least 10 wt % gives the best results. Typically, at most 15 wt % will be used.

In a typical process, a column is packed with the desired amount of active carbon (typically in granulated form), and deionized water is run through the column from top to bottom or bottom to top (downflow or upflow direction) at a flow rate that ranges from 1 to 10 bed volumes per hour. The amount of water to pass could vary from 2 to 5 bed volumes. Once the water has displaced the remaining air and some fine particulates from the carbon, the aqueous solution of the Luo Han Guo fruit extract is fed to the column at a flow rate that could range from 1 to 10 bed volumes per hour. The column should be jacketed and the jacket temperature should be maintained at the same temperature as the feed solution, which will typically be in a range from room temperature to 71° C. Initially, the feed displaces the water in the column. Once the column effluent shows signs of material present, the effluent is collected as improved taste material. The presence of solids in the effluent can be assessed by measurement of the refractive index (RI). A correlation between RI and dry substance is typically built for this purpose.

The Luo Han Guo fruit extract is fed to the column until the targeted treatment level has been reached. Once the feed ends, the remaining Luo Han Guo fruit extract still present in the column is chased with deionized or reverse osmosis water, displacing the Luo Han Guo material. The effluent collection is continued until the refractive index of the effluent is close to that of water alone.

Optionally, the recovered improved taste material can be concentrated in order to increase the DS % (dry substance) to any suitable level for subsequent drying, if desired. The concentration can be completed by evaporation or membranes, or by any other suitable method. Membrane concentration is possible with utilization of a nanofiltration membrane (200 Da. M.W.C.O.) or with a reverse osmosis membrane (with a salt rejection assay >98%). Both membranes can be used separately without losing a significant amount of mogrosides to the permeate. The material is then dried by using a conventional spray drying unit or by using a conventional spray agglomeration unit, or other means. Or the material may be used as-is. In one embodiment, the recovered improved taste material is combined with one or more other components, such as Rebaudioside A, B and/or D or a purified *Stevia* extract containing comprising sweet steviol glycosides, prior to drying.

Use of Sweetening Compositions Including Rebaudioside-Mogroside V Blends

Compositions containing Rebaudioside-Mogroside V blends may be processed using known methods to modify particle size and physical form. Methods such as agglomeration, spray-drying, drum drying and other forms of physical processing may be applied to adjust particle size in order to deliver better flow, hydration, or dissolution properties. The compositions may be provided in liquid forms, optionally containing one or more preservatives and/or processing aids, for ease-of-use in specific applications. Compositions containing Rebaudioside-Mogroside V blends may be co-processed with bulking agents such as maltodextrins and similar compounds to deliver products with controlled sweetness, dosing, potency, and handling properties.

Sweetening compositions of the present invention are useful as reduced-caloric, low-caloric, or non-caloric sweeteners in foodstuffs, i.e., edible or chewable compositions such as food, beverages, medicine, candy, chewing gum, and the like. It has been discovered that the sweetening compositions of the present invention can possess a sweetness profile that is more sugar-like and has reduced bitter aftertaste and reduced off-flavors (e.g., licorice) than sweeteners including only sweet steviol glycosides. Testing has shown that, in most cases, sweetening compositions of the present invention are preferred by test subjects over compositions that include 97% Rebaudioside A, when tested at a concentration providing equal sweetness. In particular, the sweetening compositions provide both immediate sweetness and delayed sweetness, resulting in a more satisfying flavor. Adding sweetening compositions of the present invention to foods and beverages is expected to result in better tasting foods and beverages compared to those prepared with known sweetening composition containing sweet steviol glycosides, such as compositions having 97% Rebaudioside A as the sweetener.

Sweetener compositions according to the invention may include, in addition to the Rebaudioside-Mogroside V blend, other high potency sweeteners. For example, sweet steviol glycosides may be included. Specific examples of suitable high potency sweeteners include natural high potency sweeteners such as:

dulcoside A, dulcoside B (also known as Rebaudioside C), rubusoside, mogroside III, mogroside IV, mogroside VI, siamenoside, monatin and its salts (monatin SS, RR, RS, SR), curculin, glycyrrhizic acid and its salts, thaumatin, mabinlin, brazzein, hernandulcin, phyllodulcin, glycyphyllin, and phloridzin;

and artificial high potency sweeteners such as:

saccharin, aspartame, sucralose, neotame, cyclamate and acesulfame potassium.

According to the invention, Rebaudioside-Mogroside V blends may also be combined with caloric sweeteners such as sugars (e.g., high fructose corn syrup, sucrose, fructose, etc.) and polyols (e.g., sorbitol, xylitol, lactitol, etc.) and/or other low-calorie sweeteners to produce sweetening compositions of reduced caloric value.

In some embodiments, the invention provides foodstuffs including sweetening compositions with high concentrations of Rebaudioside-Mogroside V blends. Essentially any edible or chewable composition may be sweetened in accordance with the invention. Nonlimiting examples include foodstuffs, (e.g., baked goods, soups, sauces, processed meats canned fruits, canned vegetables, dairy products, frozen confections); beverages (e.g., carbonated soft drinks, ready to drink teas, sports drinks, dairy drinks, alcoholic beverages, energy drinks, flavored waters, vitamin drinks, fruit drinks, and fruit juices, powdered soft drinks), medicines or pharmaceutical products (e.g., tablets, lozenges, suspensions, etc.), nutraceutical products (e.g., supplements, vitamins, etc.), candy or confections; chewing gum; tobacco products (e.g., chewing tobacco); and the like. The sweetening composition is included in an amount effective to impart the desired amount of sweetness to the sweetened product. In some embodiments, the pH of the sweetened product is at least about 2 and not greater than about 8.

In some embodiments, the foodstuff contains a sweetening composition including Rebaudioside-Mogroside V blends and one or more additional sweet steviol glycosides as described herein. In some embodiments, the sweetening composition inclusive of the Rebaudioside component, additional steviol glycosides components, and the Mogroside V component is present in the foodstuff at a total concentration of at least about 50 ppm, or at least about 200 ppm, or at least about 500 ppm, or at least about 1000 ppm, or at least about 1500 ppm, or at least about 3500 ppm, or at least about 5000 ppm.

EXAMPLES

Example 1—Stevia-Mogroside V Blends Vs. Rebaudioside A Preference Testing

Blends of a solid Luo Han Guo extract containing 50 wt % Mogroside V with a Stevia product containing mostly Rebaudioside A were compared in sweetness and preference panel testing against 97 wt % Rebaudioside. The Luo Han Guo extract was a purified version of a commercial product available from Biovittoria (Guilin, People's Republic of China) under the trade name Fruit Sweetness™, where the purification had been by treatment with activated carbon as described elsewhere herein to remove aromatic glycosides and semi-volatile organic compounds, which produce off-flavors. This product is identified below as Sample A. The Stevia product was a commercial product available from GLG Life Tech Corporation of Vancouver, B.C., Canada under the trade name BlendSure™ 7.5, consisting of approximately 75 wt % Rebaudioside A and 25 wt % stevioside.

Preference Testing

Paired comparison testing was conducted for sweetness and preference of blends of BlendSure 7.5 and Sample A having sweetness equal to 97% Rebaudioside A in a pH 3 citric acid buffer (0.045% citric acid and 0.013% sodium citrate) with a panel of taste testers. The tests were conducted as complete block designs with between 24 to 46 evaluations. The presentation order was rotated. The solutions were served in 2 ounce soufflé cups labeled with 3-digit codes at room temperature. The panelists were instructed to consume at least half of each sample. There was a one minute enforced waiting period between tests to clear the panelists' palates. The panelists were asked to identify the solution that was sweeter and which they liked better. Bottled water, 2% sucrose solution, and unsalted crackers were available for the panelists to clear their palates before and during testing. The sweetness results were analyzed as two-tailed tests at an alpha risk of 0.05 with the binomial test, as shown below.

The results of the sweetness and preference questions were analyzed with the binomial test and the Thurstonian d' calculated. The p-value for a one-tailed binomial test is calculated as $$1 - \sum_{k=0}^{c} \binom{n}{k} p_0^k (1-p_0)^{n-k}$$

where c is the number of successes, n is the number of trials, and $p_0$ is the chance probability. A test is considered statistically significant when the p-value is less than the a priori set alpha risk. The two-tailed p-value is double the one-tailed p-value as calculated above.

Thurstonian d' is a linear measure of psychophysical difference. A d'=1 is generally considered to be a just-noticeable-difference (JND) where a stimulus will be judged stronger in 75% of the trials. The Thurstonian d' is independent of test method and for paired comparison tests is calculated as $$p_c = \Phi(d'/\sqrt{2})$$

where $p_c$ is the proportion of successes, and $\Phi(\cdot)$ is the cumulative distribution function of the standard normal distribution. A complete treatment of these statistical calculations can be found in standard textbooks on the subject (Bi J., "Sensory Discrimination Tests and Measurements," Blackwell Publishing, 2006, Chapters 2 and 9).

Combined replicated test results are shown below in Table 1.

TABLE 1

| Samples | | | | Preference | | | Sweetness | | |
|---|---|---|---|---|---|---|---|---|---|
| Ppm Blend Sample A | Ppm Blend BlendSure | Fraction Sample A | Ppm control Reb A | Reb A Count | Blend count | p-value one-tailed | Reb A count | Blend count | p-value two-tailed |
| 444 | 296 | 0.60 | 605 | 22 | 18 | 0.68 | 16 | 24 | 0.15 |
| 547 | 365 | 0.60 | 705 | 13 | 27 | 0.01 | 15 | 25 | 0.08 |
| 547 | 365 | 0.60 | 800 | 22 | 46 | <0.01 | 24 | 44 | 0.01 |
| 547 | 365 | 0.60 | 900 | 28 | 40 | 0.06 | 45 | 23 | 0.00 |
| 660 | 440 | 0.60 | 900 | 17 | 27 | 0.05 | 15 | 29 | 0.02 |
| 660 | 440 | 0.60 | 1000 | 18 | 26 | 0.09 | 23 | 21 | 0.65 |
| 675 | 225 | 0.75 | 900 | 9 | 31 | <0.01 | 24 | 16 | 0.15 |
| 750 | 250 | 0.75 | 1000 | 12 | 28 | <0.01 | 26 | 14 | 0.04 |
| 825 | 275 | 0.75 | 1000 | 8 | 38 | <0.01 | 24 | 22 | 0.66 |

In pH 3 citric acid buffer and at sweetness levels that were not significantly different (p-value >0.05 two tailed), the above data indicate a preference for blends containing ratios of Mogroside V to Rebaudioside A within certain ranges. Specifically, the following can be seen.

A blend of 675 ppm Sample A and 225 BlendSure 7.5 (75% Sample A, 900 ppm total) was significantly preferred over 900 ppm 97% Rebaudioside A.

A blend of 825 ppm Sample A and 275 BlendSure 7.5 (75% Sample A, 1100 ppm total) was significantly preferred over 1000 ppm 97% Rebaudioside A.

A blend of 444 ppm Sample A and 296 BlendSure 7.5 (60% Sample A, 740 ppm total) was not significantly different from 605 ppm 97% Rebaudioside A.

A blend of 547 ppm Sample A and 365 BlendSure 7.5 (60% Sample A, 912 ppm total) was significantly preferred over 705 ppm 97% Rebaudioside A.

A blend of 660 ppm Sample A and 440 BlendSure 7.5 (60% Sample A, 1100 ppm total) was not significantly different in preference from 1000 ppm 97% Rebaudioside A.

Blends of Sample A and BlendSure 7.5 that contained 75% Sample A performed better than blends containing 60% Sample A against 97% Rebaudioside A.

Blends of Sample A and BlendSure 7.5 were more preferred over 97% Rebaudioside A as the level of sweetness increased.

Example 2—*Stevia*-Mogroside V Blends Vs. *Stevia* Preference Testing

Blends of a solid Luo Han Guo extract containing 50 wt % Mogroside V with a *Stevia* product containing mostly Rebaudioside A in a pH 3 citric acid buffer (0.045% citric acid and 0.013% sodium citrate) were compared in sweetness and preference panel testing against the *Stevia* product. The blends and the *Stevia* product were as described in Example 1. Synergy can be detected by the construction of isoboles (iso-effect curves) where the concentrations of two substances that have equal effect, in this case sweetness, are plotted on a chart with the axis being the concentration of the substances. Linear isoboles result when there is no synergy between the two substances. An isobole with a downward curvature results when there is synergy between the two substances. A complete discussion of isoboles and synergy can be found in Berenbaum, "What is Synergy", *Pharmacological Reviews*, Vol. 1989, No. 41 pages 93-129. Blends of BlendSure 7.5 and Sample A having sweetness equal to 500 ppm, 700 ppm, and 900 ppm BlendSure 7.5 were predicted from linear isoboles with the assumption of no sweetness synergy.

Paired comparison testing was conducted for sweetness and preference of blends of BlendSure 7.5 and Sample A that are equal sweet to levels of 500 ppm, 700 ppm, and 900 ppm BlendSure 7.5 with a panel of taste testers. The tests were conducted as complete block designs with between 34 to 44 evaluations. The presentation order was rotated. The solutions were served in 2 ounce soufflé cups labeled with 3-digit codes at room temperature. The panelists were instructed to consume at least half of each sample. There was a one minute enforced waiting period between tests to clear the panelists' palates. The panelists were asked to identify the solution that was sweeter and which they liked better. Bottled water, 2% sucrose solution, and unsalted crackers were available for the panelists to clear their palates before and during testing. The results were analyzed as in Example 1, and are summarized in Table 2.

As can be seen from the above data, there was no evidence of sweetness synergy between BlendSure 7.5 and Sample A. However, the preference for a blend of BlendSure 7.5 and Sample A over BlendSure 7.5 alone increased as the ratio of Sample A to BlendSure 7.5 increased, and also as sweetness increased.

Example 3—Removal of Aromatic Glycosides and Semi-Volatile Organic Compounds from Luo Han Guo Extract A 3'× ½" ID jacketed glass column (Ace glass incorporated) of approximately 115 ml of capacity was packed with approximately 57 g of virgin granular active carbon (CAL 12×40 from Calgon Corporation) that had been freshly washed with boiling water. The column jacket was heated to 60° C. and held at that temperature during the duration of the experiment. After packing the column, approximately 500 mL of deionized water was passed through the carbon bed at a flow rate of 2.5 mL/min in order to displace and remove carbon lines. A 27% % wt solution of Biovittoria Fruit Sweetness™ (approximately 50 wt % Mogroside V dry solids basis (dsb)) was prepared by dissolving 1.241 kg of Biovittoria Fruit Sweetness™ in 3.318 kg of Milli-Q water (water provided by a Milli-Q reverse osmosis water purification system, available from Millipore Corp.). The solution was then heated to 60° C., passed through a Millipore Optiseal Durapore 0.22 µm hydrophilic pleated cartridge filter to a sterile feed bottle and held at 60° C. during the run.

The solution was passed through the column at a rate of 2.6 g/min (equivalent to 1.25 Bed volumes per hour) using MASTERFLEX® tubing 13 and a peristaltic pump (MASTERFLEX® pump). The effluent was collected in 90 minute fractions, with an average mass of 234 grams per fraction. After fraction 19 (elapse run time: 28.5 hours), the effluent was tasted and it was informally determined that the effluent had a significantly better taste than the feed material. Therefore, an additional 355.5 g of Biovittoria Fruit Sweetness™ was dissolved in 945.3 g of Milli-Q water, brought up to 60° C., passed through a Millipore Optiseal Durapore 0.22 µm hydrophilic pleated cartridge filter, and added to the feed bottle. After 37.5 hours, the sweeten-off (the term "sweeten off" is understood as washing the column for displacement of remaining Fruit Sweetness™ solution) was started by changing the column feed to Milli-Q water (@ 60° C.). The column was allowed to sweeten off for 6 hours until the refractive index of the effluent was similar to that of water. The material collected in all fractions corresponded to an overall mass yield of approximately 98 wt % of the dry

TABLE 2

| Samples | | | | Preference | | | Sweetness | | |
|---|---|---|---|---|---|---|---|---|---|
| Ppm Blend Sample A | Ppm Blend BlendSure | Fraction Sample A | Ppm control BlendSure | BlendSure count | Blend count | p-value one-tailed | BlendSure count | Blend count | p-value two-tailed |
| 133 | 399 | 0.25 | 500 | 38 | 43 | 0.51 | 44 | 37 | 0.37 |
| 284 | 284 | 0.50 | 500 | 32 | 49 | 0.04 | 41 | 40 | 0.82 |
| 458 | 153 | 0.75 | 500 | 13 | 31 | <0.01 | 20 | 24 | 0.45 |
| 660 | 0 | 1.00 | 500 | 29 | 52 | 0.01 | 35 | 46 | 0.18 |
| 179 | 537 | 0.25 | 700 | 33 | 46 | 0.11 | 50 | 29 | 0.01 |
| 367 | 367 | 0.50 | 700 | 23 | 56 | <0.01 | 33 | 46 | 0.11 |
| 563 | 188 | 0.75 | 700 | 23 | 56 | <0.01 | 38 | 41 | 0.65 |
| 770 | 0 | 1.00 | 700 | 32 | 47 | 0.07 | 43 | 36 | 0.37 |
| 226 | 679 | 0.25 | 900 | 24 | 48 | <0.01 | 39 | 33 | 0.41 |
| 455 | 455 | 0.50 | 900 | 22 | 50 | <0.01 | 34 | 38 | 0.56 |
| 686 | 229 | 0.75 | 900 | 23 | 49 | <0.01 | 40 | 32 | 0.29 |
| 920 | 0 | 1.00 | 900 | 19 | 53 | <0.01 | 37 | 35 | 0.72 | material fed to the apparatus. The treatment level of the total material feed to the apparatus (1241 g+335 g) was calculated to be 3.61 wt %. A Roundtable of eight experience tasters compared acceptability in regard to reduced off-flavor by comparing water solutions of Fruit Sweetness™, Composite of fractions 1 through 5, Composite of fractions 1 through 10, Composite of fractions 1 through 15, Composite of fractions 1 through 20, and Composite of fractions 1 through 25. It was found that the Composites of 1 through 5, 1 through 10 and 1 through 15 presented a significant level of taste improvement over the Fruit Sweetness™ feed material. A Composite of fractions 1 through 15 contained a dry mass of 947 g, thus corresponding to a carbon treatment level of 6.0 wt %. The Composite of fractions 1 through 15 was henceforth identified as SAMPLE A (286683).

HPLC was used to determine the aromatic glycoside composition of the Biovittoria Fruit Sweetness™ feed and better tasting Luo Han Guo effluent after carbon treatment. A Waters 2695 Separations Module was equipped with a Waters 2487 Dual λ Absorbance Detector and a Phenomenex Gemini C18 Column, 5 μm, 150×4.6 mm with Phenomenex Gemini C18 Security Guard cartridge, 4×3 mm. An acetonitrile/water gradient listed below was used as the mobile phase, at a flow rate of 10.0 mL/min and a column temperature of 40° C. UV detection at 203 nm was used, and the injection volume of 40 μL.

| Mobile Phase: Acetonitrile/Water volume % linear segment gradient | | |
|---|---|---|
| Time [min] | Acetonitrile | H$_2$O |
| 0 | 20 | 80 |
| 15 | 30 | 70 |
| 20 | 50 | 50 |
| 25 | 50 | 50 |
| 30 | 20 | 80 |

A pure Mogroside V standard (ChomaDex, Inc.) was used for calibrated quantitation of all components detected at 203 nm. Table 3 summarizes the wt % of components on a dry solids basis (d.s.b) as Mogroside V. A significant reduction of aromatic glycosides eluting from the HPLC column in the range of 3.5 to 4.5 minutes under the above defined conditions was observed between the Biovittoria Fruit Sweetness™ feed and the carbon effluent, and this reduction corresponded to the as noted significant flavor improvement.

TABLE 3

| Sample ID | Mog V wt % of total sample dsb | Aromatic glycosides wt % of total sample as Mog V | Aromatic glycosides wt % relative to Mog V |
|---|---|---|---|
| Biovittoria Fruit Sweetness™ feed (284178) | 49.1% | 7.3% | 14.8% |
| Luo Han Guo Sample A (286683) | 50.9% | 4.2% | 8.3% |

Headspace GC with Flame Ionization detection (FID) as defined by the following conditions was used to determine the composition of semi-volatile organic compounds in the Luo Han Guo feed and the better tasting Luo Han Guo recovered after carbon treatment.

Combi PAL Autosampler
　Mode: Headspace
　Syringe Volume: 1 mL
　Syringe Temperature: 85° C.
　Agitator Temperature: 80° C.
　Pre-incubation Time: 30 minutes
　Pre-incubation Agitator Speed: 500 rpm (5 sec on, 2 sec off)
　Plunger Fill Speed: 200 μL/sec
　Viscosity Delay: 12 sec
　Pre-injection Delay: 0 sec
　Plunger Inject Speed: 100 μL/sec
　Post-injection Delay: 10 sec
　Syringe Flush Time: 3 min
　GC Cycle Time: 54 min
Varian 3800 GC
　Oven:
　Initial Temperature: 40° C.
　Initial Hold Time: 5 minutes
　Ramp: 7.5° C./min
　Final Temperature: 235° C.
　Final Hold Time: 14 minutes
　Front Inlet (1177):
　Temperature: 250° C.
　Mode: Splitless
　Column:
　Type: Rtx-624 (30 m×0.25 mm×1.4 μm) Restek Cat #10968
　Mode: Constant Flow
　Flow: 1.0 mL/min (Helium)
　Middle Valve Oven:
　Temperature: 250° C.
Varian 4000 FID
　Temperature: 250° C.
　Makeup gas: 2 mL/min (He)
　H$_2$ flow: 40 mL/min
　Air flow: 450 mL/min
Varian 4000 Ion Trap MS
　Scan Type: Full
　Mass Range: 25-275 m/z
　Scan Time: 0.00 to 45.00 minutes
　Ionization Type: EI
　Target TIC: 20000 counts
　Max Ion Time: 25000 μsec
　Emission Current: 10 μamps
　Scans Averaged: 3 μscans (0.60 sec/scan)
　Data Rate: 1.67 Hz
　Multiplier Offset: 0 V A pure D-limonene standard (Sigma-Aldrich) was used for calibrated quantitation of all semi-volatile organic compound components shown in FIG. 3. Table 4 summarizes the total semi-volatile organic compounds ppm wt of components on a dry solids basis (dsb) as D-limonene. A significant reduction of semi-volatile organic compounds from Biovittoria Fruit Sweetness™ feed (284178) to carbon treated Luo Han Guo (Sample A 286683) is seen, corresponding to the significant improvement of Luo Han Guo flavor.

TABLE 4

| Sample ID | Mog V wt % of total sample dsb | Semi-volatile organic compounds ppm wt as D-limonene of total sample | Semi-volatile organic compounds ppm wt relative to Mog V |
|---|---|---|---|
| Biovittoria Fruit Sweetness™ feed (284178) | 49.1% | 8.9 | 18 |

TABLE 4-continued

| Sample ID | Mog V wt % of total sample dsb | Semi-volatile organic compounds ppm wt as D-limonene of total sample | Semi-volatile organic compounds ppm wt relative to Mog V |
|---|---|---|---|
| Luo Han Guo Sample A (286683) | 50.9% | 0.6 | 1.2 |

Example 4—Identification of Off-Flavor Components in Luo Han Guo Extract

Sensory evaluation has found that Luo Han Guo material that has passed through carbon in aqueous solution has a better, more acceptable flavor than the feed Luo Han Guo material. HPLC analysis of an exemplary dry Luo Han Guo extract having a Mogroside V content of about 50 wt % (Biovittoria Fruit Sweetness™), and analysis of the same material that had been carbon treated and spray dried, are shown in the upper and lower chromatograms respectively in FIG. 1. The HPLC method parameters were as in Example 3 with the following modified linear segment gradient.

| Mobile Phase: Acetonitrile/Water volume % linear gradient | | |
|---|---|---|
| Time [min] | Acetonitrile | H$_2$O |
| 0 | 10 | 90 |
| 10 | 10 | 90 |
| 20 | 20 | 80 |
| 25 | 20 | 80 |
| 30 | 30 | 70 |
| 35 | 30 | 70 |
| 55 | 95 | 5 |
| 65 | 95 | 5 |
| 75 | 10 | 90 |

Figure 2:
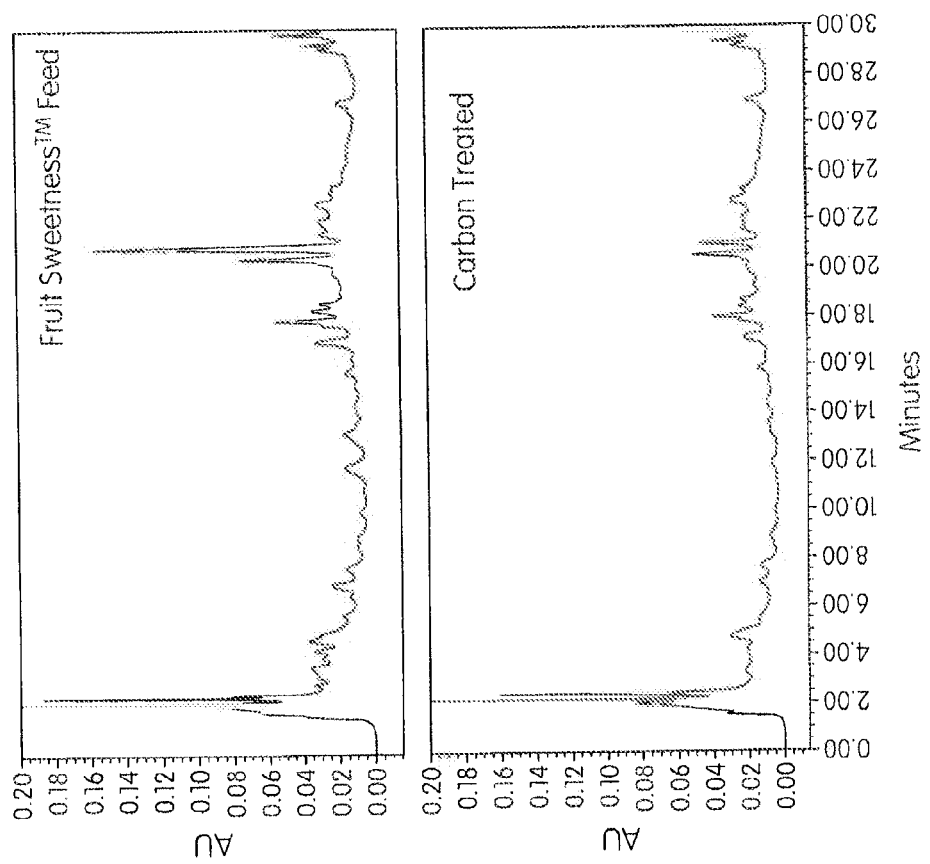
FIG. 2 shows enlarged views of the chromatograms shown in FIG. 1.

HPLC analysis showed that the profile of mogroside isomers remained essentially unchanged after carbon treatment. An enlarged view of the more polar region of the chromatograms of FIG. 1 is shown in FIG. 2, where the treated product shown in the lower chromatogram shows peaks in the vicinity of 21 min (marked with an arrow) greatly decreased relative to the untreated product in the upper chromatogram. In order to determine the relationship of the component(s) eluting near 21 min and the decrease in "musty" off-flavor, a series of extraction and purification steps was applied to spent carbon that had been used to treat Luo Han Guo in a manner similar to Example 3. After each extraction purification step throughout this study, an expert panel of tasters evaluated the samples of carbon treated Luo Han Guo that had been spiked with ~5-10× of the original level of the recovered components in order to identify the samples which exhibited the characteristic "musty" off-flavor of Fruit Sweetness™.

To recover components removed by carbon treatment of aqueous Luo Han Guo solution approximately 500 g of spent carbon that had been used for Luo Han Guo refinement was sequentially extracted with multiple 350 mL aliquots of solvents after water washing. Ethanol and then acetone were used to wash the carbon. The extracts were filtered through a 0.45 μm nylon filters and evaporated to dryness under a stream of nitrogen at ambient temperature to recover approximately 2.0 g of solid. The residue from the acetone extract was observed by the aforementioned expert panel of tasters to contain the significant "musty" off-flavor characteristic of Fruit Sweetness™. It was also confirmed that the 21 min HPLC component (FIGS. 1 and 2) was contained in the acetone fraction and also in all subsequent "musty" off-flavor fractions, as described below.

Liquid-liquid extraction between 50 mL water and 50 mL chloroform was applied to the initial acetone extracted fraction after complete drying. The "musty" off-flavor remained with the water soluble fraction (approximately 1.8 g of solid recovered). Subsequently, solid phase extraction (SPE) using four stacked Waters Sep-Pak C18 SPE cartridges (Waters Corp., WAT020515) was applied to further fractionate the off-flavor residue. Approximately 10 mg/mL residue in water was loaded onto the cartridges 10 mL at a time after conditioning the SPEs with 5 mL of methanol and 10 mL of Milli-Q water. Recovered fractions were then obtained using a series of 10 mL SPE washes as follows; 100% water, 2% acetonitrile (MeCN)/98% water, 5% MeCN, 10% MeCN, 20% MeCN, 25% MeCN, 30% MeCN, 40% MeCN, 50% MeCN, and 100% MeCN. All extracts were dried under a stream of nitrogen and evaluated by a sensory panel. This entire isolation procedure from spent carbon through to SPE fractionation was repeated three times with the same sensory results.

The characteristic "musty" off-flavor was determined to be significantly concentrated in the approximately 250 mg of solids recovered from the 20% MeCN/80% water eluted SPE fraction (288054) as verified by the expert panel of tasters when spiked into a water solution of carbon treated Luo Han Guo. HPLC of this fraction again showed the 21 min eluting component, FIG. 4. Chemical analyses of the primary components of this isolate, relative to an SPE blank (10 mL water+10 mL 50% MeCN+10 mL 100% MeCN) were conducted using; Antek total nitrogen, Folin-Ciocalteu phenolic colorimetric test, ninhydrin protein colorimetric test, ion chromatography amino acid analysis of an acid digest, ATR-FTIR of dry solid, LC-MS, and NMR. Results are summarized in Tables 5 and 6, and are consistent with an aromatic glycoside class of compounds,

TABLE 5

Figure 5:
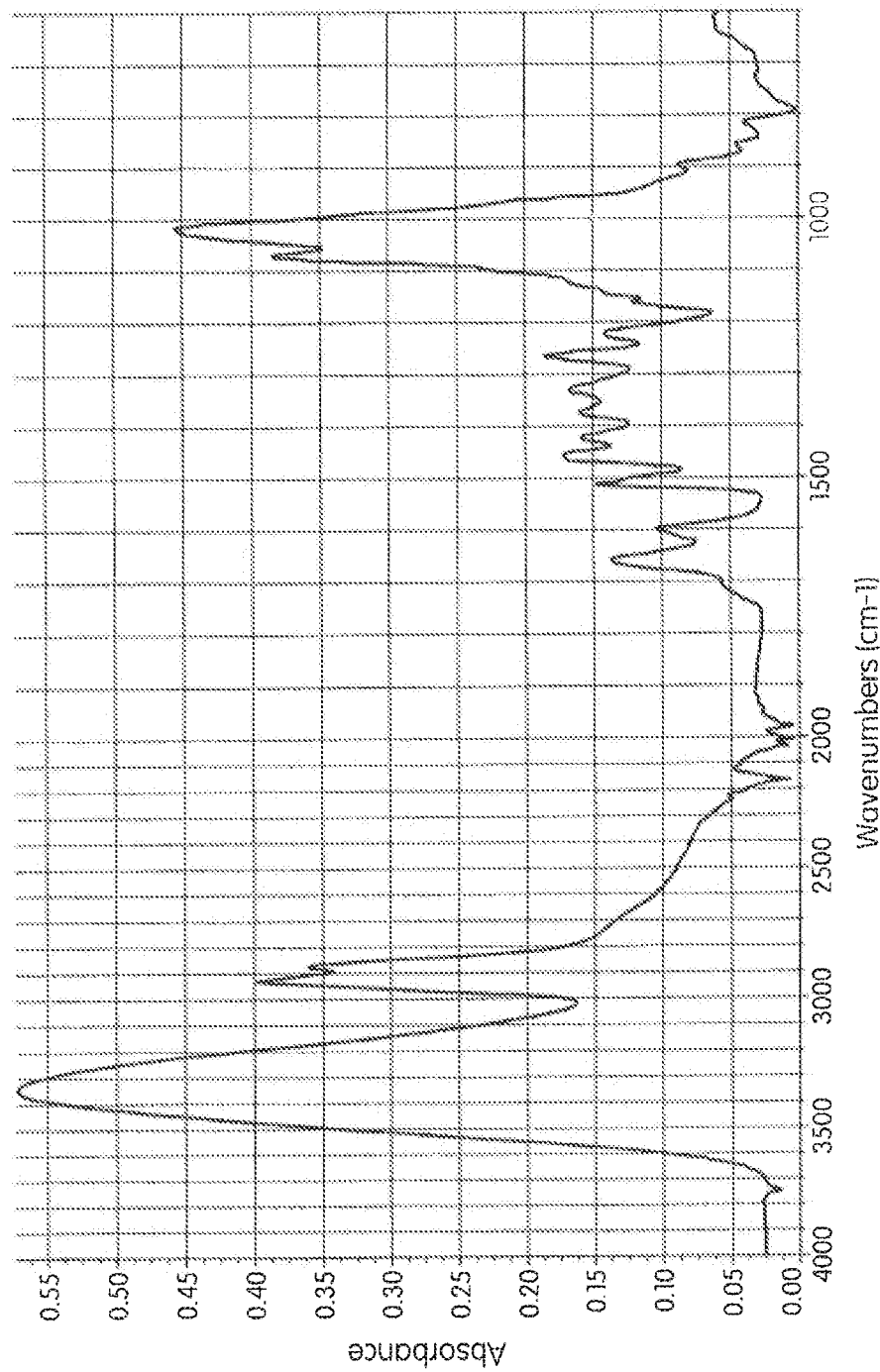
FIG. 5 shows an ATR-FTIR spectrum of a Luo Han Guo fraction showing characteristic bands consistent with the presence of an aromatic glycoside.
Figure 6:
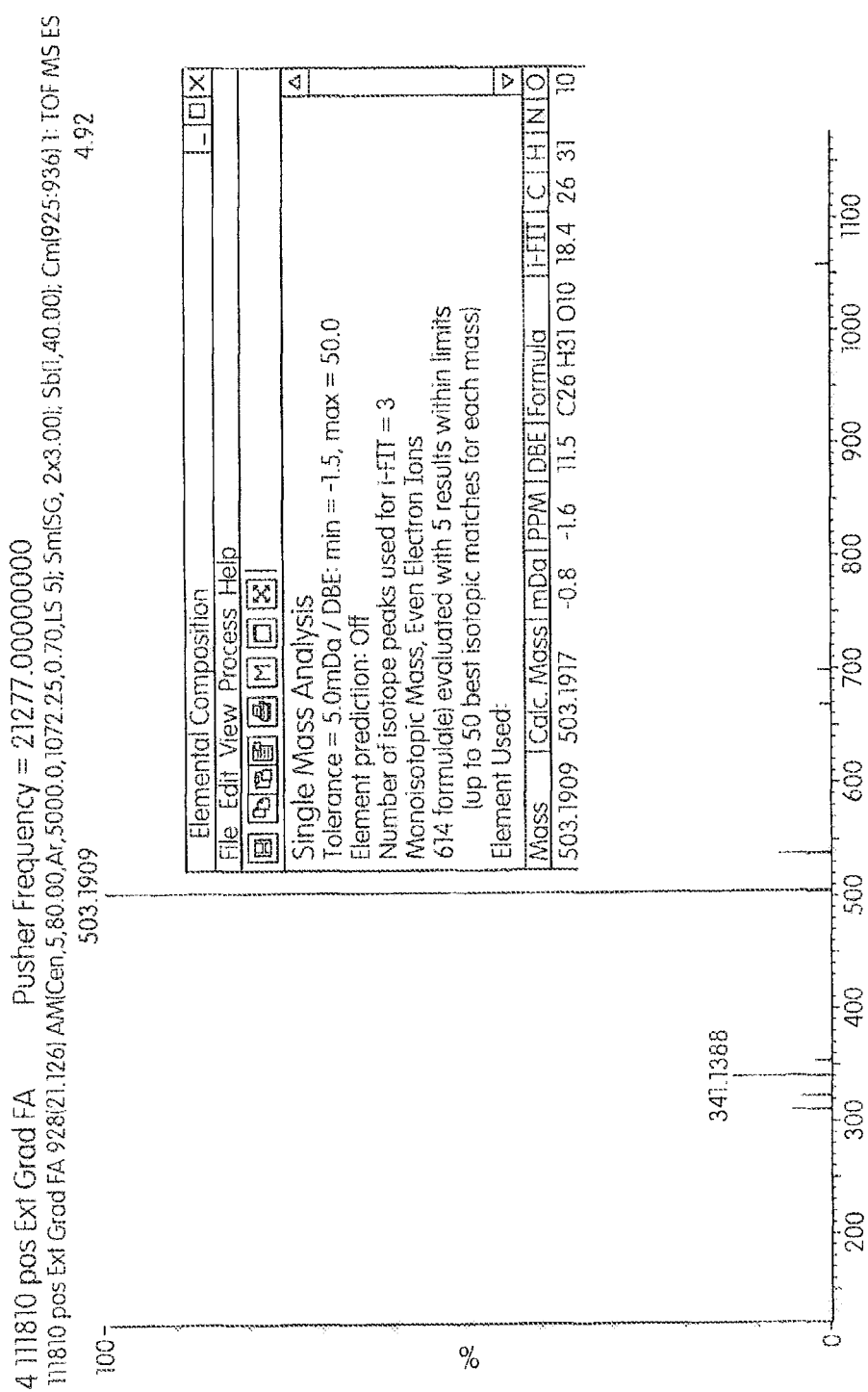
FIG. 6 shows a Time-of-Flight (ToF) accurate Mass Spectrum for the major component in FIG. 4.

| Test | 288054 - SPE 20% MeCN |
|---|---|
| Folin-Ciocalteu phenolics expressed as gallic acid equivalents | 17.6 mg/mL |
| Ninhydrin protein color test | Yellow (minimal protein) |
| Antek total nitrogen | 0.4% wt |
| IC Amino acids | 2.4% wt as protein |
| ATR-FTIR | FIG. 5 |
| LC-MS | FIG. 6 |
| H-NMR, $^{13}$C-NMR, COSY-45, DEPT-135 | Table 5 |

FIG. 5 shows the baseline corrected ATR-FTIR. spectrum of fraction 288054. Characteristic bands for OH, aliphatic CH, CO, and weak phenyl absorbances can be seen, all consistent with the presence of an aromatic glycoside. No C═O absorbance is observed.

Figure 4:
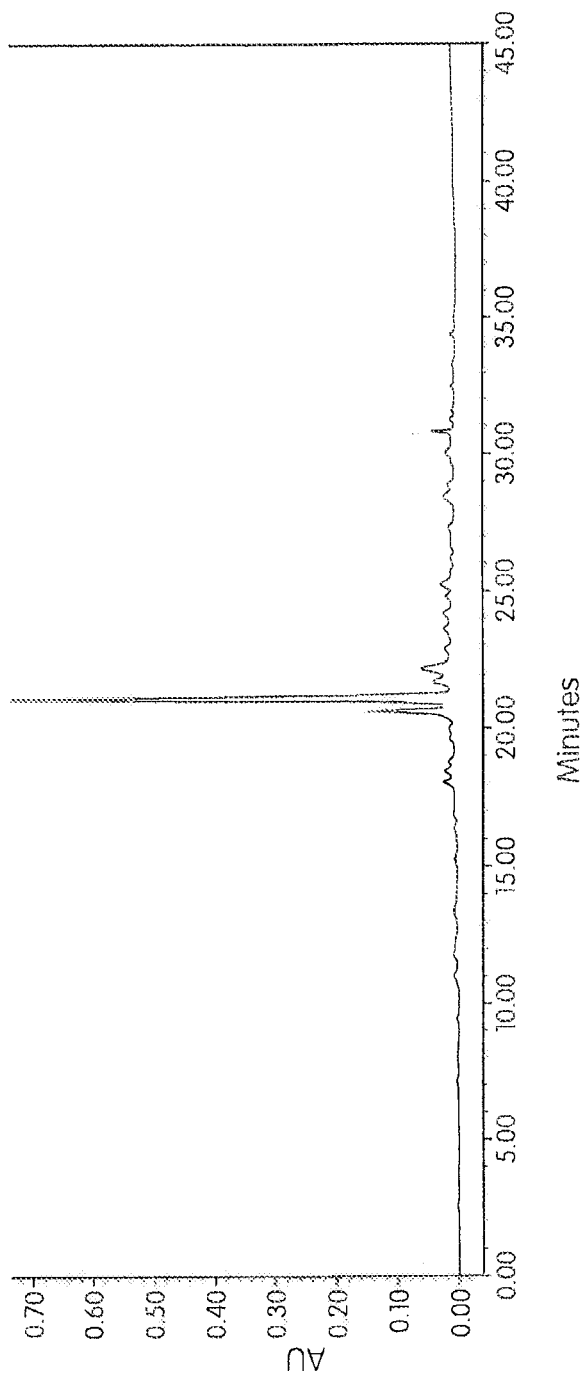
FIG. 4 shows an HPLC chromatogram of a fraction of Luo Han Guo containing components producing a musty flavor.

FIG. 6 shows the Time-of-Flight (ToF) accurate Mass Spectrum for the major component corresponding to sample 288054 in FIG. 4 with retention time of 21.0 minutes. The inserted table in FIG. 6 lists the most probable stoichiometric formula for mass ion 503 Daltons. The most probable accurate mass with 1.6 ppm mass accuracy is shown to be a $C_{26}H_{30}O_{10}$ neutral charge compound.

TABLE 6

| NMR measurement for sample 288054 | NMR shift resonances | Structural sub-unit information |
|---|---|---|
| ¹H-NMR | 5.6 ppm and 5.1 ppm doublets typical on anomeric protons; multiple resonances between 3.9 ppm and 3.3 ppm | Glycoside sub-units |

TABLE 6-continued

| NMR measurement for sample 288054 | NMR shift resonances | Structural sub-unit information |
|---|---|---|
| ¹H-NMR | multiple resonances between 6.85 to 7.10 ppm | Substituted aromatic rings |
| COSY-45 | | Connectivities consistent with glycosidic proton resonances |
| COSY-45 | 3.75, 3.8 ppm | Methoxy subunits |
| ¹³C/DEPT-135 | resonances for methines 101, 75 to 70 ppm; and methylenes 61 to 63 ppm. | Glycoside sub-units |
| ¹³C/DEPT-135 | resonances for methines 119, 116, 111 ppm; phenoxy methyl resonance 53.7 ppm | Substituted aromatic rings; Aromatic methoxy sub-units |

Figure 3:
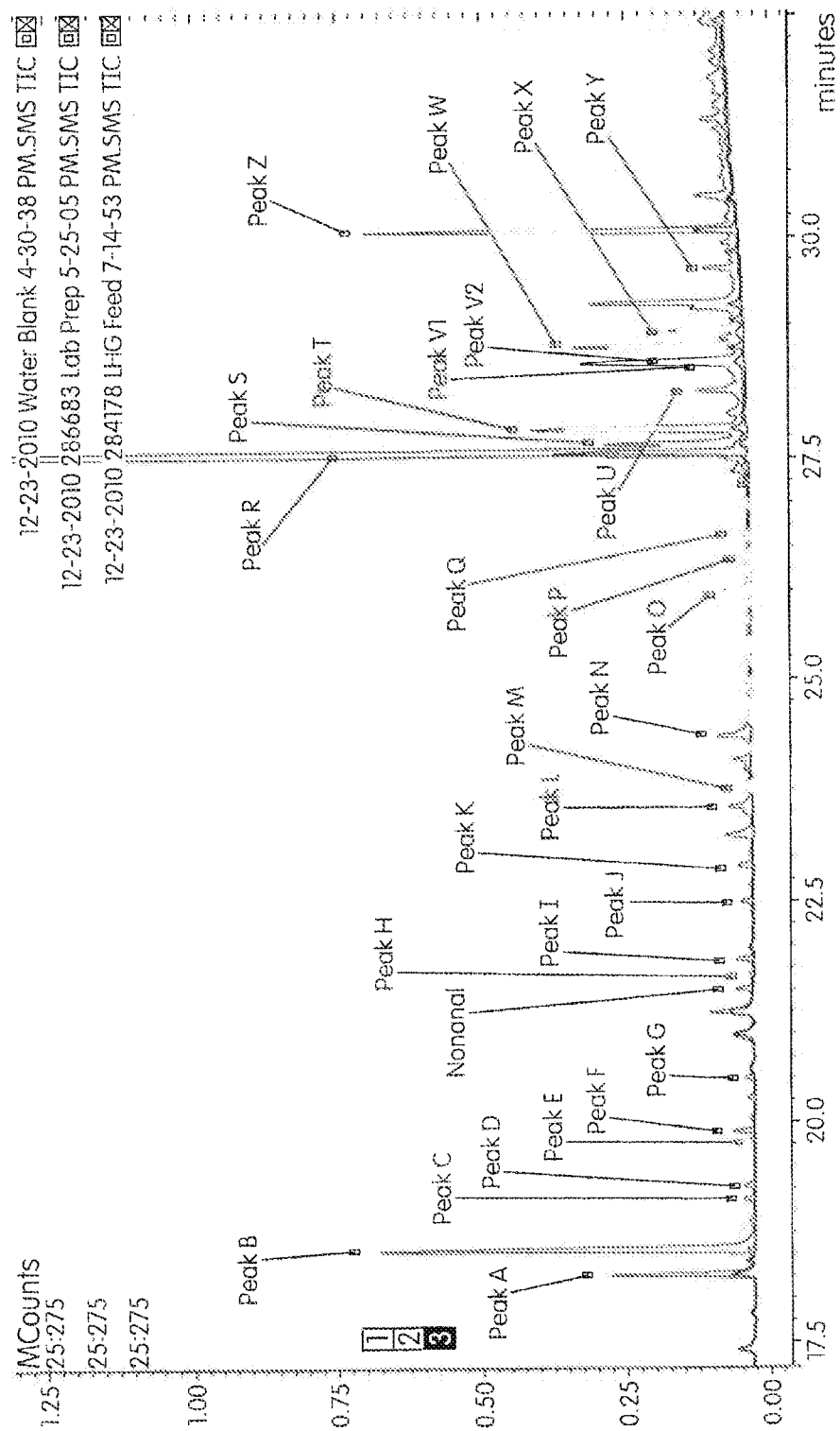
FIG. 3 shows gas chromatograms of semi-volatile organic compounds present in a sample of Luo Han Guo, one taken before treatment with activated carbon and one after treatment with activated carbon according to the invention.

The distribution and suggested identity of a variety of semi-volatile components was evaluated using headspace of 5% aqueous solutions via Gas Chromatography with mass spectrometric detection (GC-MS) as defined in Example 3. FIG. 3 shows a comparison of the semi-volatile component profile of Fruit Sweetness™ feed (284178) and Sample A. Table 7 shows a listing of best MS library matches for 28 semi-volatile organic compounds corresponding to those labeled in FIG. 3. Known flavor and odor organoleptic responses to these compounds are listed for comparison (see for example, Mosciano, G., Perfumer and Flavorist 25, No. 6, 26, (2000).

TABLE 7

| Peak ref. (FIG. 3) | Component name (CAS#) | Known organoleptic response |
|---|---|---|
| A | 2-pentyl-furan (3777-69-3) | Green, waxy, with musty, cooked caramellic nuances |
| B | Butyl butanoate (109-21-7) | Sweet, fresh, fruity, slightly fatty |
| C | D-limonene (5989-27-5) | Sweet, orange, citrus and terpy |
| D | t-butylbenzene (98-06-6) | — |
| E | Gamma-terpinene (99-85-4) | Terpy, citrus, lime-like, oily, green with a tropical fruity nuance |
| F | Butyl butenoate (7299-91-4) | — |
| G | Terpinolene (586-62-9) | Citrus, Lime, Pine, plastic |
|   | Nonanal (75718-12-6) | — |
| H | Durene (95-93-2) | — |
| I | 1,3,8-p-menthatriene (21195-59-5) | — |
| J | p-cymene (99-87-6) | Terpy and rancid with slightly woody oxidized citrus notes |
| K | Hexyl butyrate (2639-63-6) | Apple, Fruity, Green, Soapy, Sweet |
| L | 1,1,5,6-Tetramethylindane (942-43-8) | — |
| M | Azulene (275-51-4) | — |
| N | α-ionene (475-03-6) | — |
| O | 1-methyl-naphthalene (90-12-0) | Naphthyl-like with a medicinal nuance |
| P | 2-methyl-naphthalene (91-57-6) | — |
| Q | dehydro-ar-ionene (30364-38-6) | licorice |
| R | (−)-α-Cedrene (469-61-4) | woody cedar |
| S | Z-β-farnesene (28973-97-9) | citrus green |
| T | (+)-β-Cedrene (546-28-1) | — |
| U | Trans-α-bergamotene (13474-59-4) | woody |
| V1 | cis-α-bisabolene (29837-07-8) | — |
| V2 | α-farnesene (502-61-4) | Fresh green vegetative, with celery and hay nuances and somewhat fatty and tropical fruity afternotes |
| W | (−)-β-bisabolene (495-61-4) | balsamic |
| X | (+)-α-Longipinene (5989-08-2) | — |
| Y | 2-hexyl-1-dodecanol (2425-77-6) | — |
| Z | (E)-Nerolidol (40716-66-3) | green floral woody fruity citrus melon |

Example 5

An amount of 40 g of Fruit Sweetness™ was dissolved in 200 g of Milli-Q water in a 500-mL beaker and 30 g of activated carbon (BG-HHM from Calgon Carbon Corporation) was added to the Fruit Sweetness™ solution. The activated carbon slurry was stirred for 2 hours, while taking 50 µL samples of sterile filtered solution at 0, 5, 15, 30, 60, 90, and 120 minutes. The samples were diluted 20-fold in Milli-Q water and analyzed by HPLC for relative abundance of mogrosides between time points. After 2 hours, the activated carbon slurry was filtered through Whatman #2 filter paper and the filtrate was sterile filtered into a tared freeze drying bottle. Once the sterile filtrate had been freeze dried, its mass was recorded and analyzed with HPLC for Mogroside V content. The freeze-dried material was designated Sample B. A 550 ppm neutral pH water solution of Sample B (carbon slurry treated Fruit Sweetness™) was then tested against 500 ppm Reb A 97 in neutral pH water for taste preference by 48 to 50 panelists. For comparison, the Fruit Sweetness™ was also tested against 500 ppm Reb A 97 for preference in neutral pH water. The tests were conducted as complete block designs. The presentation order was rotated. The solutions were served in 2 ounce soufflé cups at room temperature. The panelists were instructed to consume all of the sample. The panelists were not allowed to retaste the samples. The panelists were asked to identify the solution that was sweeter and which they preferred. Bottled water, 2% sucrose solution, and unsalted crackers were available for the panelists to clear their palates before and during testing.

The data were analyzed with the binomial test with an alpha risk of 0.05 as two-tailed tests for sweetness and a one-tailed test for preference.

TABLE 8

|  | Preference | | Sweetness | |
| --- | --- | --- | --- | --- |
|  | count | One-tailed p-value | count | Two-tailed p-value |
| 500 ppm Reb A 97 | 22 | 0.24 | 22 | 0.47 |
| 550 ppm Fruit Sweetness ™ | 26 |  | 26 |  |

TABLE 9

|  | Preference | | Sweetness | |
| --- | --- | --- | --- | --- |
|  | count | One-tailed p-value | count | Two-tailed p-value |
| 500 ppm Reb A 97 | 6 | <0.01 | 21 | 0.20 |
| 550 ppm Sample B | 44 |  | 29 |  |

Table 8 shows that the commercial product Fruit Sweetness™ was not significantly preferred over Reb A at equi-sweetness level. However, the slurry carbon-treated Fruit Sweetness™ Sample B was significantly preferred over BlendSure 7.5 at equi-sweetness level (Table 9).

Although the invention is illustrated and described herein with reference to specific embodiments, the invention is not intended to be limited to the details shown. Rather, various modifications may be made in the details within the scope and range of equivalents of the claims without departing from the invention.

What is claimed is:

1. A method of purifying a Luo Han Guo extract comprising contacting the Luo Han Guo extract with granular activated carbon having a surface area of over 100 $m^2/g$, wherein the Luo Han Guo extract that is contacted is in the form of an aqueous solution and is one that has previously been contacted with at least one of an ion exchange resin or a macroporous polymeric adsorbent resin, and wherein the aqueous solution is passed through a column of the granular activated carbon at a flow rate of from 1 to 10 bed volumes per hour and wherein the Luo Han Guo extract is contacted with an amount of the granular activated carbon for a contact time effective to reduce the levels of aromatic glycoside and semi-volatile organic compound impurities present in the Luo Han Guo extract.

2. The method of claim 1, wherein the Luo Han Guo extract that is contacted is one that has previously been contacted with a macroporous polymeric adsorbent resin.

3. The method of claim 1, wherein the Luo Han Guo extract that is contacted is one that has been previously contacted with both a macroporous polymeric adsorbent resin and an ion exchange resin.

4. The method of claim 1, wherein the Luo Han Guo extract that is contacted is one that has been previously contacted with first a macroporous polymeric adsorbent resin and then an ion exchange resin.

5. The method of claim 1, wherein the Luo Han Guo extract that is contacted is one that has previously been contacted with an ion exchange resin that is an anionic resin.

6. The method of claim 1, wherein the Luo Han Guo extract contacted with activated carbon has been prepared by dissolving a powdered dry extract of Luo Han Guo fruit in water to obtain a dissolved extract.

7. The method of claim 6, wherein the dissolved extract is subjected to microfiltration.

8. The method of claim 1, wherein an effluent is obtained as a result of passing the aqueous solution through the column of granular activated carbon, and wherein the effluent is subsequently concentrated.

9. The method of claim 8, wherein the effluent is concentrated by evaporation or membrane concentration.

10. The method of claim 8, wherein the effluent is concentrated by membrane concentration using a nanofiltration membrane or a reverse osmosis membrane.

11. The method of claim 8, wherein following concentration the effluent is dried.

12. The method of claim 11, wherein the effluent is dried using a spray drying unit or a spray agglomeration unit.

13. The method of claim 8, wherein following concentration the effluent is combined with one or more components selected from the group consisting of Rebaudioside A, Rebaudioside B, Rebaudioside D, Steviol glycoside and purified Stevia extract and then dried.

14. The method of claim 1, wherein contacting the Luo Han Guo extract with activated carbon removes pesticide residues from the Luo Han Guo extract.

15. The method of claim 1, wherein water is the only carrier present during the contacting of the Luo Han Guo extract with the activated carbon.

16. A method of purifying a Luo Han Guo extract comprising a) contacting the Luo Han Guo extract sequentially with a macroporous polymeric adsorbent resin, an anionic ion exchange resin and activated carbon, wherein an aqueous solution of the Luo Han Guo extract is passed through a column of granular activated carbon having a surface area of over 100 $m^2/g$ at a flow rate of from 1 to 10 bed volumes per hour and a temperature of from room temperature to 71° C., wherein prior to passing the aqueous solution through the column deionized water is run through the column, whereby the levels of aromatic glycoside and semi-volatile organic compound impurities and pesticide residues present in the Luo Han Guo extract are reduced, thereby obtaining an effluent, and b) drying the effluent using a spray drying unit or a spray agglomeration unit.

17. The method of claim 1, wherein the aqueous solution being fed to the column is at a temperature of from room temperature to 71° C., wherein the column is jacketed and wherein the jacket is maintained at the same temperature as the temperature of the aqueous solution being fed to the column.

18. The method of claim 1, wherein prior to passing the aqueous solution through the column deionized water is run through the column.

19. The method of claim 1, wherein prior to passing the aqueous solution through the column deionized water is run through the column at a flow rate of 1 to 10 bed volumes per hour.

20. The method of claim 1, wherein prior to passing the aqueous solution through the column 2 to 5 bed volumes of water is passed through the column.

* * * * *